United States Patent [19]
Shiho et al.

[11] Patent Number: 5,625,123
[45] Date of Patent: Apr. 29, 1997

[54] NEUROTROPHIN-3-DEFICIENT EMBRYONIC STEM CELLS AND MICE AND THEIR USE

[75] Inventors: Osamu Shiho, Takashima-gun; Yoshihiko Kaisho, Sakai; Hideaki Tojo, Kobe, all of Japan

[73] Assignee: Takeda Chemical Industries, Ltd., Osaka, Japan

[21] Appl. No.: 268,020

[22] Filed: Jun. 29, 1994

[30] Foreign Application Priority Data

Jul. 6, 1993 [JP] Japan .................................. 5-166936
Jan. 19, 1994 [JP] Japan .................................. 6-003824
Jun. 23, 1994 [JP] Japan .................................. 6-141858

[51] Int. Cl.$^6$ .......................... A61K 49/00; C12N 15/00; C12N 15/06; G01N 31/00
[52] U.S. Cl. .................... 800/2; 424/9.2; 435/172.3
[58] Field of Search ................. 800/2; 435/69.1, 435/72.3; 424/9.1, 9.2; 935/70, 71, 34

[56] References Cited

FOREIGN PATENT DOCUMENTS

| | | |
|---|---|---|
| 0386752 | 9/1990 | European Pat. Off. |
| 0582796 | 2/1994 | European Pat. Off. |
| WO91/03569 | 3/1991 | WIPO |
| WO92/18149 | 10/1992 | WIPO |

OTHER PUBLICATIONS

Y. Kaisho, et la. "Cloning and expression of a cDNA encoding a novel human neurotrophic factor" FEBS Letters, vol. 266/1,2, 187–191 (1990).

M. Kuehn, et al. "A potential animal model for . . . " Nature, vol. 326, pp. 295–298 (1987).

Dominic Cosgrove et al. "Mice Lacking MHC Class II Molecules" Cell, vol. 66, 1051–1066, Sep. 6, 1991.

Alcino J. Silva, et al. "Deficient Hippocampal . . . ", Science, vol. 257 pp. 201–206, Jul. 10, 1992.

Kevin R. Jones, "Targeted Disrupton of the BDNF Gene . . . " Cell, vol. 76 989–999, Mar. 25, 1994.

Craig Crowley, et al. "Mice Lacing Nerve Growth Factor . . . " Cell, vol. 76 1001–1011, Mar. 25, 1994.

Patrik Ernfors, et al. "Mice lacking brain-derived . . . " Nature, vol. 368 pp. 147–150, Mar. 10, 1994.

Farinas, et al., Nature, vol. 369:658 (Jun. 23, 1994) "Severe sensory and sympathetic deficits in mice lacking Neurotrophin-3".

Ernfors, et al., Cells, vol. 77:503 (May 20, 1994) "Lack of Neurotrophin-3 Leads to Deficiencies in the Peripheral Nervous System and Loss of Limb Proprioceptive Afferents".

Bradley et al., 1992. Biotechnology, 10:534–539.
Zimmer et al. 1992. Annu. Rev. Neurosci. 15:115–137.
Le Monellic et al. 1990. Proc. National Academy of Science, USA 87:4712–4716.

Primary Examiner—Brian R. Stanton
Attorney, Agent, or Firm—David G. Conlin; David S. Resnick; Dike, Bronstein, Roberts & Cushman, LLP

[57] ABSTRACT

The present invention provides mouse embryonic stem cells and homozygous mutant mice carrying disruptions in the neurotrophin-3 (NT-3) gene generated by homologous recombination which results in the insertion of a reporter gene or a drug-resistance gene into an exon of the neurotrophin-3 gene. The mice harboring such homozygous mutations have a reduced number of sensory neurons compared with the number of sensory neurons present in a mouse lacking such mutations. These mice may be used to screen for substances that enhance the transcriptional activity of the NT-3 gene.

7 Claims, 5 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
       ( A ) LENGTH: 25 base pairs
       ( B ) TYPE: nucleic acid
       ( C ) STRANDEDNESS: single
       ( D ) TOPOLOGY: linear ( i i ) MOLECULE TYPE: other nucleic acid ( i v ) ANTI-SENSE: no ( x i ) SEQUENCE DESCRIPTION: SEQ ID NO:1:

CAGCCCTACA GCCACATGAT ATCTT                                              25

( 2 ) INFORMATION FOR SEQ ID NO:2:

( i ) SEQUENCE CHARACTERISTICS:
       ( A ) LENGTH: 25 base pairs
       ( B ) TYPE: nucleic acid
       ( C ) STRANDEDNESS: single
       ( D ) TOPOLOGY: linear ( i i ) MOLECULE TYPE: other nucleic acid ( i v ) ANTI-SENSE: yes ( x i ) SEQUENCE DESCRIPTION: SEQ ID NO:2:

ACTCCAGTCT TGCCTGTATG TGATG                                              25

( 2 ) INFORMATION FOR SEQ ID NO:3:

( i ) SEQUENCE CHARACTERISTICS:
       ( A ) LENGTH: 45 base pairs
       ( B ) TYPE: nucleic acid
       ( C ) STRANDEDNESS: single
       ( D ) TOPOLOGY: linear ( i i ) MOLECULE TYPE: Other nucleic acid ( i v ) ANTI-SENSE: yes ( v ) FRAGMENT TYPE: Internal fragment ( v i ) ORIGINAL SOURCE:
       ( A ) ORGANISM: mouse
       ( B ) STRAIN: mouse trkC cDNA ( x i ) SEQUENCE DESCRIPTION: SEQ ID NO:3:

GATCTCAGTC TTGCTGCAGA CACAATTTGC AGGGCAAGCC AGCAC                        45

( 2 ) INFORMATION FOR SEQ ID NO:4:

( i ) SEQUENCE CHARACTERISTICS:
       ( A ) LENGTH: 45 base pairs
       ( B ) TYPE: nucleic acid
       ( C ) STRANDEDNESS: single
       ( D ) TOPOLOGY: linear ( i i ) MOLECULE TYPE: Other nucleic acid ( i v ) ANTI-SENSE: yes ( v ) FRAGMENT TYPE: Internal fragment ( v i ) ORIGINAL SOURCE:

(A) ORGANISM: mouse
(B) STRAIN: mouse trkC cDNA (xi) SEQUENCE DESCRIPTION: SEQ ID NO:4:

TGTGGTGAGC CGGTTACTTG ACAAGTTTAT ATAACGCAAG TGGGG                    45

(2) INFORMATION FOR SEQ ID NO:5:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: Other nucleic acid (iv) ANTI-SENSE: yes (v) FRAGMENT TYPE: Internal fragment (vi) ORIGINAL SOURCE:
(A) ORGANISM: mouse
(B) STRAIN: mouse trkC cDNA (xi) SEQUENCE DESCRIPTION: SEQ ID NO:5:

CAAAGGAGAG CCAGAGCCAT TGCAAGTGAT CACGGCATTG TCTCC                    45

(2) INFORMATION FOR SEQ ID NO:6:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: Other nucleic acid (iv) ANTI-SENSE: no (v) FRAGMENT TYPE: Internal fragment (vi) ORIGINAL SOURCE:
(A) ORGANISM: rat
(B) STRAIN: rat trkC cDNA (xi) SEQUENCE DESCRIPTION: SEQ ID NO:6:

AGCGTCTGGC TGGACTATGT GGGGCT                                        26

(2) INFORMATION FOR SEQ ID NO:7:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Other nucleic acid (iv) ANTI-SENSE: yes (v) FRAGMENT TYPE: Internal fragment (vi) ORIGINAL SOURCE:
(A) ORGANISM: rat
(B) STRAIN: rat trkC cDNA (xi) SEQUENCE DESCRIPTION: SEQ ID NO:7:

GGTGACTATC CAGTCCACAT CA                                            22

NEUROTROPHIN-3-DEFICIENT EMBRYONIC STEM CELLS AND MICE AND THEIR USE

FIELD OF THE INVENTION

The present invention relates to a non-human mammalian embryonic stem cell wherein the neurotrophin-3 (hereinafter also referred to as NT-3) gene is inactivated, and a non-human mammal deficient in NT-3 expression.

BACKGROUND OF THE INVENTION

With the advance in developmental engineering technology and the rapid compilation of knowledge in molecular biology, it has become possible to artificially manipulate genes and introduce them to animal individuals [Gordon, J. W. et al., Proceedings of National Academy of Science, U.S.A., Vol. 77, pp. 7380–7384, (1980)]. Thanks to development of various methods of artificially adding exogenous gene essentially not conferred upon the organism of interest, or artificially suppressing expression of endogenous genetic characters essentially conferred upon the organism, a variety of transgenic animals have been generated and reported.

Such transgenic animals are important in clarifying the functions of various cloned genes isolated by gene engineering and other technologies, since they enable research on an individual basis in the functional analysis of genes, regarding which information availability has been limited due to the fact that only cells cultured in vitro, such as cultured cells or primary cultured cells, have been available. Analysis of the physiological functions of cloned genes in vivo, and in particular experiments and studies using such transgenic animals as models of genetic diseases are actively being undertaken.

Embryonic stem cells (ES cells) of a strain established from an inner cell mass of the blastocyst, or the fertilized embryo at the early stage, are capable of being grown and cultured with keeping in an undifferentiated state. These cells possess multipotency, by which they can differentiate into every kind of cell; when injected to a normal early stage embryo, they can participate in embryo formation to form a chimeric animal [Evans M. J. and Kaufman M. H., Nature, Vol. 292, p. 154 (1981)].

Making use of such nature, there have been attempts at creating various gene mutant animals. This trend dates back to 1981, when the ES cell line was established by Evans and Kaufman, followed by extensive research starting at the creation of an ES chimeric mouse by Bradley et al. [Nature, Vol. 309, p. 255 (1984)]. As successful achievements were reported, including homologous recombination in ES cells by Thomas and Capecchi [Cell, Vol. 51, p. 503 (1987)] and subsequent germ line transmission of ES cells by three research groups, including that of Koller et al. [Proceedings of National Academy of Science, U.S.A., Vol. 86, p. 8927 (1989)], there have been rapid advances in the generation of gene-deficient mice and in research using them.

In addition to the EK cells of Evans and Kaufman (ibid.), established ES cell lines reported so far include the ES-D3 cells of Doetschman [Journal of Embryology and Experimental Morphology, Vol. 87, p. 27 (1981)], the CCE cells of Robertson [Nature, Vol. 323, p. 445 (1986)] and the BL/6 III cells of Ledermann and Burki [Experimental Cell Research, Vol. 197, p. 254], most of which have been established from 129 strain mouse embryos. Despite the very high value of use in gene targeting, which modifies a particular gene, and for other purposes, ES cells are now subject to limitation as to applicability because their establishment, and their passage while in an undifferentiated state, are difficult. To make routine the creation of animal disease models using ES cells, it is necessary to develop a system for constantly establishing and supplying good ES cells.

Animals deficient in gene expression generated using such ES cells include the HPRT-gene-deficient mouse generated using a spontaneously mutated ES cell by Hooper et al. [Nature, Vol. 326, p. 292 (1987)] and Knehn et al. [Nature, Vol. 326, p. 295 (1987)], the p53-deficient mouse, which lacks p53, a tumor suppressor gene, generated by Donehower et al. [Nature, Vol. 356, p. 215 (1992)], the β2-microglobulin gene mutant mouse generated by Zijlstra et al. [Nature, Vol. 344, p. 742 (1990)], the RAG-2 (V(D)J recombination activation gene) mutant mouse, an immune disease model mouse, generated by Sinkai et al. [Cell, Vol. 68, p. 855 (1992)], the MHC class II mutant mouse generated by Glimcher et al. [Science, Vol. 253, p. 1417 (1991)] and Cosgrove et al. [Cell, Vol. 66, p. 1051 (1991)], the int-1-deficient mouse, a development/growth-related disease model mouse generated by MacMahon et al. [Cell, Vol. 62, p. 1073 (1990)], and the src-deficient mouse, which develops symptoms like those of marble bone disease, generated by Soriano et al. [Cell, Vol. 64, p. 693 (1991)].

The neurotrophins comprise factors with sequence similarity [e.g., nerve growth factor (NGF), brain-derived neurotrophic factor (BDNF), neurotrophin-3 (NT-3), NT-4 and NT-5]. Since the discovery of NGF by Levi-Monntalchini [Annual of New York Academy of Science, 55, 330 (1952)] and Cohen et al. [Proceedings of National Academy of Science, U.S.A., Vol. 40, p. 1014 (1954)], BDNF [Barde Y-A et al., EMBO Journal, Vol. 1, pp. 549–553 (1982)], NT-3 [Hohn et al., Nature, Vol. 344, p. 399 (1990); PCT Patent Publication No. WO91/03569], NT-4 [Neuron, Vol. 6, p. 845 (1991)] and NT-5 [Neuron, Vol. 7, p. 857 (1991)] have been reported one by one, drawing attention from those searching for preventive or therapeutic measures against diseases of the cranial nervous system, particularly dementia.

These factors have been found to play various role such as nerve cell differentiation, maturation, survival, functional retention and proliferation, and are classified under a single family because they are structurally similar to each other. They are known to show distinct patterns of expression during stages of development, and to act on different types of cells while sharing a role in the survival of several kinds of primary culture nerve cells. Concerning their actions, it is known that NGF shows activities on peripheral sympathetic nerve cells and septal cholinergic nerve cells, and that BDNF acts on motor nerve cells and midbrain dopaminergic nerve cells. As for actions on other factors and cells of non-nerve tissue, much remains unknown, though NGF is known to promote peripheral lymphocyte colony formation.

As for NT-3, human nerve growth factor 2 (NGF-2), identical to NT-3, is disclosed as a polypeptide (I) in European Patent Publication No. 386,752, and reported in FEBS Letters, Vol. 266, pp. 187–191 (1990). It is known that (1) it expresses markedly in the kidney, cerebral hippocampus and cerebellum, (2) it expresses more strongly in neonates than in mature animals, and (3) it acts on nerve cells on which NGF and BDNF show little or no activity (e.g., nerve cells of nodose ganglion origin). These facts suggest that NGF-2/NT-3 plays an important role in the development of the nervous system. Also, this factor has recently been shown to promote human peripheral lymphocyte colony formation, suggesting that it also plays an important role in the growth of leukocytes, neutrophils etc. However, much remains to be clarified as to the function of NT-3 in vivo, including these actions. Although an animal model deficient

3 in NT-3 expression (which produces no NT-3, or only a trace amount) is desirable as a model for elucidation of the factions of NT-3 in vivo, no such animal models have been generated.

SUMMARY OF THE INVENTION

The present invention relates to non-human NT-3 deficient embryonic stem cells (ES cells). The present invention further relates to a non-human NT-3 deficient mammal produced using the ES cells. The present invention also relates to a method for screening a substance capable of enhancing the NT-3 promotor using the non-human animal model.

BRIEF DESCRIPTION OF THE DRAWINGS

V: EcoRV, Bg: BglII, P: PstI, N: NotI, ATG: Translation initiation codon, pA: PolyA additional signal

DETAILED DESCRIPTION OF THE INVENTION

Through extensive investigation aiming at solving the above problems, the present inventors succeeded in establishing ES cell lines, capable of chimera formation, from early stage embryos of the BDF1 (C57BL/6× DBA/2) mouse and C57BL/6 mouse, respectively, both cultured in a medium containing human leukemia inhibitory factor (LIF) in an mount more than 5 times the usual amount, with STO cells of mouse fetal fibroblast origin, which produce LIF and are resistant to neomycin and hygromycin [The New Biologist, Vol. 3, p. 861 (1991)] as feeder cells, and confirmed that these ES cells are capable of forming germ cell line chimeras at high rates. The inventors also generated mice deficient in the NT-3 gene by homologous recombination of genes using established ES cell lines. The inventors made further investigations based on these findings, and developed the present invention.

Accordingly, the present invention provides a non-human mammalian embryonic stem cell wherein the neurotrophine-3 gene (NT-3) is deficient, specifically carries Escherichia coli β-galactosidase gene and/or is resistant to neomycin and/or which is the embryonic stem cell of rodent, especially a mouse. The present invention further provides a non-human mammal deficient in neurotrophine-3 expression, specifically the animal being capable of producing foreign protein or polypeptide encoded by reporter gene such as Escherichia coli β-galactosidase, the animal preferably being a rodent, especially a mouse. The present

4 invention also provides a method of screening a substance capable of enhancing the NT-3 promoter which comprises administering a sample to be tested to the mammal and detecting expression of Escherichia coli derived β-galactosidase.

In the present specification, the non-human mammalian embryonic stem cell (ES cell) wherein the NT-3 gene is disrupted is defined as a non-human mammalian ES cell, wherein the NT-3 gene substantially lacks NT-3 expression as a result of suppression of gene expression capability or substantial elimination of the activity of the NT-3 protein, by artificial mutation of the NT-3 genomic gene of said non-human mammal (hereinafter also referred to as the NT-3 disrupted gene). For animal model establishment, the non-human mammal is preferably a rodent such as a mouse or rat, characterized by short cycles of individual development and life and relatively easy propagation; examples include, but are not limited to, rabbits, pigs, sheep, goats and bovines.

Artificial mutagenesis in the NT-3 genomic gene includes partial or total deletion of the relevant gene sequence, addition of another gene or replacement with another gene by conventional genetic engineering techniques. Using these mutagenesis techniques, the NT-3 gene can be disrupted by such as shifting a frame-work or disabling the promoter.

Specifically, the ES cells of the present invention, wherein the NT-3 gene is disrupted (NT-3 disrupted ES cells), can be obtained by, for example, isolating the desired non-human mammalian NT-3 genomic gene, introducing a DNA fragment having a DNA sequence constructed by inserting a drug resistant gene, such as the neomycin resistant gene or the hygromycin resistant gene, or a reporter gene such as lacZ (β-galactosidase gene) or cat (chloramphenicol acetyl-transferase gene) to an exon thereof to disable the exon, or integrating to a chromosome of the subject animal by, e.g., homologous recombination, a DNA sequence which terminates gene transcription (e.g., polyA additional signal) in the intron between exons to inhibit the synthesis of complete messenger RNA and hence destroy the gene (hereinafter referred to as targeting vector). The thus-obtained ES cells to Southern hybridization analysis with a DNA sequence on or near the NT-3 gene as a probe, or to PCR analysis with a DNA sequence on the targeting vector and another DNA sequence near the NT-3 gene which is not included in the targeting vector as primers, to select ES cells with the targeted mutation. In this operation, the NT-3 genomic gene can be isolated using known methods such as the plaque hybridization method with a known cDNA sequence such as the already-reported human NT-3 cDNA sequence [FEBS Letters, Vol. 266, p. 187 (1990)] as a probe.

The parental ES cells to disrupt the NT-3 gene by homologous recombination etc. may be of a strain already established as described above, or may be originally established in accordance with the known method of Evans and Kaufman supra. For example, in the case of mouse ES cells, it is common practice to use ES cells of the 129-strain mouse. However, since their immunological background is obscure, the C57BL/6 mouse or the BDF1 mouse (F1 hybrid between C57BL/6 and DBA/2), wherein the low ovum availability per animal in the C57BL/6 mouse has been improved by crossing with DBA/2, may be preferably used instead to obtain a pure line of ES cells of clear immunological genetic background and for other purposes. The BDF1 mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days post coitum are commonly used; in the present invention, embryos are preferably collected at the 8-cell stage, cultured until the blastocyte stage and used to efficiently obtain a large number of early stage embryos.

Although the ES cells used may be of either sex, male ES cells are more convenient for generation of a germ cell line chimera and are therefore preferred. It is desirable that sexes be differentiated as soon as possible to save painstaking culture time.

Methods of ES cell sex identification include the method in which a gene in the sex-determining region on the Y-chromosome is amplified by the PCR process and detected. When this method is used, 1 colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture. Second selection can be achieved by, for example, number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., mouse cells having 40 chromosomes) after the gene is disrupted.

Although the embryonic stem cell line thus obtained shows very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and 90% air) in the presence of LIF (1–10000 U/ml) on appropriate feeder cells such as STO fibroblasts, treated with a trypsin/EDTA solution (normally about 0.001 to about 0.5% trypsin/about 0.1 to about 5 mM EDTA, preferably about 0.1% trypsin/1 mM EDTA) at the time of passage to obtain separate single cells, which are then seeded on freshly prepared feeder cells. This passage is normally conducted every 1 to 3 days; it is desirable that cells be observed at passage and morphologically abnormal cells in culture, if any, be abandoned.

Both alleles of ES cells can be disrupted by two targeting vectors with different types of drug resistant markers. The ES cell line having a null mutation, thus generated, is useful to examine the function of the disrupted gene in vitro. If ES cells are allowed to reach a high density in mono-layers or to form aggregates in suspension, they will spontaneously differentiate to various cell types, for example pariental and visceral endoderm, cardiac muscle and other unidentified cell types (M. J. Evans and M. H. kaufman, Nature, 292, 154, 1981; G. R. Martin, Proc. Natl. Acad. Sci. U.S.A., 78, 7634, 1981; T. C. Doetschman et al., J. Embryol. Exp. Morphol., 87, 27, 1985). The NT-3 deficient cells are useful for studying the function of NT-3 cytologically or molecular biologically.

The non-human NT-3 deficient mammal of the present invention is a non-human mammal wherein by NT-3 gene disruption NT-3 gene expression is decreased below 50% of that of a normal animal in that species, as can be differentiated by measuring the mRNA amount in the subject animal by a known method, as described in Reference Examples below, and indirectly comparing the degrees of expression. For generation of a pathologic animal mode, the non-human mammal is preferably a rodent such as a mouse or rat, characterized by short cycles of ontogeny and life, and relatively easy propagation; examples include, but are not limited to, rabbits, pigs, bovines, goats, sheep, dogs and cats.

With respect to the non-human NT-3 deficient mammal of the present invention, the NT-3 gene can be disrupted by introducing a targeting vector, prepared as described above, to non-human mammal embryonic stem cells or oocytes thereof, and conducting homologous recombination in which a targeting vector DNA sequence, wherein NT-3 gene is disrupted upon introduction, is replaced with the NT-3 gene on a chromosome of a non-human mammal embryonic stem cell or embryo thereof. The NT-3 gene disrupted cells can be identified by Southern hybridization analysis with a DNA fragment on or near the NT-3 gene as a probe, or by PCR analysis using a DNA sequence on the targeting vector and another DNA sequence which is not included in the targeting vector as primers. When non-human mammalian embryonic stem cells are used, a cell line wherein the NT-3 gene is disrupted by homologous recombination is cloned; the resulting cloned cell line is injected to e.g., a non-human mammalian embryo or blastocyst at an appropriate stage such as the 8-cell stage. The resulting chimeric embryos are transplanted to the uterus of the pseudopregnant non-human mammal. The resulting animal is a chimeric animal composed of both cells having the normal NT-3 gene locus and those having a mutated NT-3 gene locus. When some germ cells of the chimeric animal have a mutated NT-3 gene locus, an individual whose entire tissue is composed of cells having a mutated NT-3 gene locus can be selected from a series of offsprings obtained by crossing between such a chimeric animal and a normal animal, by genotype analysis such as Southern blotting etc. The individuals thus obtained are heterozygous for this mutation, individuals homozygous for this mutation can be obtained from offspring of the intercross between heterozygotes.

When an one-cell embryo is used, a DNA solution may be injected to the prenucleus by microinjection to obtain a transgenic non-human mammal having a targeting vector introduced in a chromosome thereof. From such transgenic non-human mammals, those having a mutation at the NT-3 gene locus can be obtained by selection based on homologous recombination.

Individuals wherein the NT-3 gene is disrupted permit breeding under ordinary rearing conditions, after individuals resulting from crossing thereof have proven to have the disrupted gene. A mutated offspring may be obtained and maintained by conventional methods. Specifically, by crossing male and female animals each having the disrupted gene, homozygote animals having the disrupted gene in both loci can be obtained. The homozygotes thus obtained may be reared so that one normal animal and two or more homozygotes are produced from a mother animal, as shown in Example 5 below, to efficiently obtain such homozygotes. By crossing male and female heterozygotes, homozygotes and heterozygotes having the disrupted gene are proliferated and passaged.

The non-human mammalian embryonic stem cell of the present invention, wherein the NT-3 gene is inactivated, is very useful in generating a non-human mammal deficient in NT-3 expression. The non-human mammal such as mouse of the present invention, deficient in NT-3 expression, can serve as an animal model of diseases caused by neuropathies of the peripheral nerves such as sensory nerves and motor nerves, or central nervous neuropathies, including learning disability and cerebellar dysfunction, since it spontaneously develops such neuropathies, lacking potential for differentiation into various nerve cells, i.e., the function of NT-3 to promote elongation of nerve projections and maintain their survival. The mouse of the present invention is therefore useful in elucidating causes of such diseases and developing therapies, and can be used in, for example, studies of the effect of psychotropic agents. Lacking functions such as human peripheral lymphocyte colony formation promotion and fibroblast growth promotion, the mouse of the present invention offers potential as a disease model of leukocyte maturation deficiency, leukopenia or organ sclerosis.

The present invention is hereinafter described in more detail by means of the following examples, which are not to be construed as limitative to the present invention.

Abbreviations for nucleotides, amino acids, solvents and others used in the present specification, and drawings attached thereto, are based on abbreviations specified by the IUPAC-IUB Commission on Biochemical Nomenclature or abbreviations in common use in relevant fields. Some examples are given below. When an optical isomer may be present in amino acid, it is of the L-configuration, unless otherwise stated. These abbreviations may represent residues of corresponding compounds capable of forming a peptide bond.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTrP: Deoxythymidine triphosphate
dGTP: Deoxyguanosine triphosphate
dCTP: Deoxycytidine triphosphate
ATP: Adenosine triphosphate
EDTA: Ethylenediaminetetraacetic acid
SDS: Sodium dodecyl sulfate
Gly or G: Glycine
Ala or A: Alanine
Val or V: Valine
Leu or L: Leucine
Ile or I: Isoleucine
Ser or S: Serine
Thr or T: Threonine
Cys or C: Cysteine
Met or M: Methionine
Glu or E: Glutamic acid
Gln or Q: Glutmine
Asp or D: Aspartic acid
Lys or K: Lysine
Arg or R: Arginine
His or H: Histidine
Phe or F: Phenylalanine
Tyr or Y: Tyrosine
Trp or W: Tryptophan
Pro or P: Proline
Ash or N: Asparagine Reference Example 1 Measurement of Gene Expression Tissue from a non-human mammal (mouse) was washed with 5.0 ml of cold phosphate buffered saline (PBS), and all RNA was isolated by the modified CsCl density gradient method as described by Chirgwin et al. in Biochemistry, Vol. 18, p. 5294 (1979). The prepared RNA pellets were reprecipitated in ethanol and washed once. Next, poly(A) RNA was concentrated using oligo-dT-cellulose by the method of Aviv et al. [Proceedings of National Academy of Science, U.S.A., Vol. 69, p. 1408 (1972)], and finally recovered by ethanol precipitation. Poly(A) RNA, taken from each tissue, was electrophoresed on 1% formaldehyde-1.5% agarose gel, transfected to a nylon filter and treated by the method described by Thomas [Proceedings of National Academy of Science, U.S.A., Vol. 77, p. 75201 (1980)]. The filter was then subjected to overnight hybridization with $^{32}$P-labeled-DNA probe containing the mouse NT-3 gene sequence, twice washed with 2×SSC and 0.1% SDS at room temperature and then once washed with 0.1×SSC and 0.1% SDS at 65° C. The washed filter was applied to an appropriate analyzer such as FUJI BAS2000 to visualize and quantitate the bands from respective hybrids to determine the mount of gene expression.

Reference Example 2 Preparation of Feeder Cells for ES Cells

STO cells, as feeder cells, were cultured in Dulbecco's modified Eagle medium (DMEM, Nissui Pharmaceutical Co., Ltd.) containing 10% fetal bovine serum (FBS, Flow) and 0.1 mM non-essential amino acids (NEAA, GIBCO) (hereinafter referred to as STO cell culture medium). When about 70–80% confluence was reached just before full confluence, mitomycin C (Kyowa Hakko Kogyo Co., Ltd.) was added to the medium to a final concentration of 10 µg/ml; the cells were cultured at 37° C. for 2.5 hours and then twice washed with Dulbecco's phosphate-buffered saline (PBS(–)) containing 1 mM EDTA. After the cells were treated with 1 mM EDTA-PBS(–) containing 0.025% trypsin to yield a single-cell suspension, medium was added, followed by centrifugation at 200×g for 5 minutes and cell harvesting.

The cells were suspended in STO cell culture medium to a concentration of 2×10$^5$ cells/ml. The resulting cell suspension, in amounts of 1 ml, 2 ml, 3 ml or 10 ml, was added to 24-well Linbro culture plates or 35 mm, 60 mm or 100 mm petri dishes (Falcon), previously coated with 0.1% gelatin solution (Sigma), to yield feeder cells in a monolayer.

Reference Example 3 Sex Identification of ES Cells

One colony of ES cells (about 50 cells) was transferred to an Eppendorf tube and incubated at 37° C. overnight or at 55° C. for 90 minutes in 100 µl of a cell lysis buffer containing 600 µg/ml proteinase K (Sigma) to lyse, after which they were heated at 95° C. for 10 minutes to inactivate the proteinase K, followed by centrifugation at 1,400×g for 5 minutes. After the supernatant was transferred to a new tube, followed by ethanol precipitation, the precipitate was again dissolved in distilled water. Using a one-fourth amount as a PCR template and 5'>CAGCCCTACAGCCA-CATGATATCTT<3' (Sry-3) (SEQ ID NO. 1) and 5'>ACTC-CAGTCTTGCCTGTATGTGATG<3' (Sry-4) (SEQ ID NO. 2), both synthesized on the basis of the reported base sequence of the Sry gene (431 bp) [Hogan B. et al., Manipulating the Mouse Embryo: An Experiment Manual, published by Cold Spring Harbor Laboratories] as PCR primers, PCR was conducted in which preheating at 94° C. for 5 minutes was followed by 40 cycles of heating at 94° C. for 30 seconds and at 60° C. for 1 minute and 30 seconds, and subsequent finishing extension at 72° C. for 5 minutes; the sample was examined for amplification of the 431 bp DNA fragment.

Example 1 Establishment of ES Cell Line

To female BDF1 and C57BL/6 mice, 5 IU of pregnant mare's serum serotropin (PMS, Teikoku Hormone Manufacturing Co., Ltd.) was intraperitoneally administered. Forty-six to 48 hours later 5 IU of human chorionic gonadotropin (hCG, Teikoku Hormone Manufacturing Co., Ltd.) was intraperitoneally administered to induce superovulation. The mice were laparotomized 2.5 days after crossing with male mice of the same line; 8-cell embryos were collected by uterine perfusion and cultured overnight on a gelatinized 24-well Linbro culture plate containing an LIF-free ES cell culture medium [ESM: DMEM (Nissui Pharmaceutical Co., Ltd.) containing 20% inactivated FBS (Flow), 0.1 mM NEAA, 1.0 mM sodium pyruvate (Flow), 0.1 mM 2-mercaptoethanol (2-ME, Sigma), 0.1 mM nucleoside (Sigma) and recombinant mouse LIF (rmLIF) (1×10$^3$ U/ml, AMRAD)].

Embryos reaching the blastocyst stage were collected by a glass capillary, and seeded over feeder cells, as described in Reference Example 2, on ESM supplemented with LIF at $5\times10^3$ U/ml, an amount 5 times the ordinary amount. When the trophectoderm was broken and the inner cell mass grew, the inner cell mass was collected by aspiration in a glass capillary, prepared as a single-cell suspension in a droplet of 1 mM EDTA-PBS(−) containing 0.025% trypsin, and again seeded over feeder cells. When the number of cells in the cell mass increased to about 100, the DNA fragment on the sex-determining region of the Y-chromosome, Sry was amplified by the PCR process, and detected to select for cells of the male karyotype. The selected cells were seeded over feeder cells via trypsin-EDTA treatment every 2–3 days, and subcultured while increasing the culture scale. When the cell count increased to about $10^6$ cells/ml, the chromosomes were counted by the G-banding method; male cells having 40 chromosomes (normal number) were selected and immediately freezed-in DMEM containing 10% FBS and 10% dimethylsulfoxide (Sigma) as a freezing medium, to prevent cell deterioration. ES cell lines BDM-3 and BDM-5 were thus obtained.

Example 2 Construction of Targeting Vector pNT3LNT

1) A mouse genomic gene library (BALB/c) was screened by the plaque hybridization method with a reported human NT-3 cDNA [FEBS Letters, Vol. 266, p. 187 (1990)] as a probe, to obtain the mouse NT-3 genomic gene as a 15 kb SalI fragment.

Figure 1:
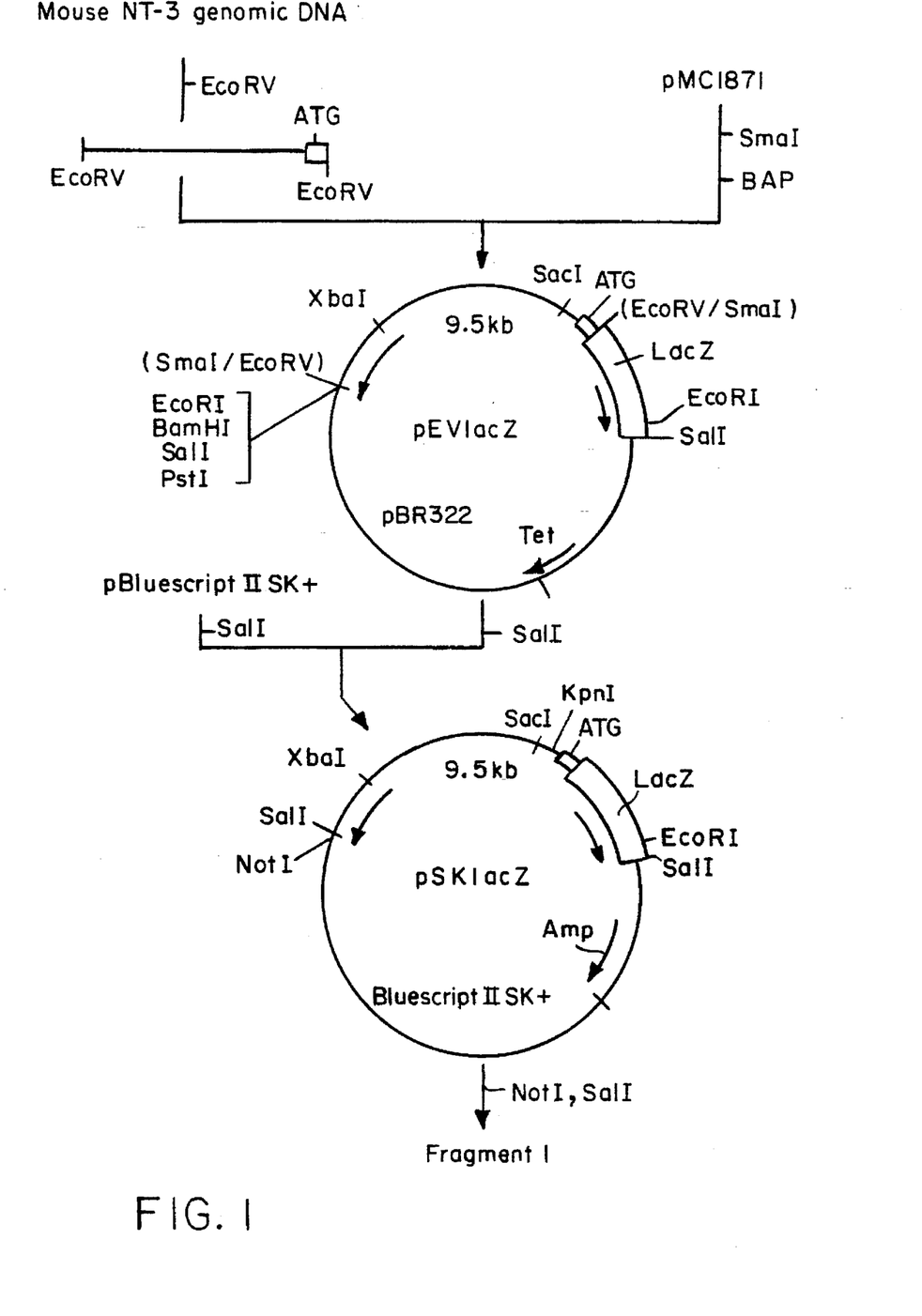
FIGS. 1 to 4 show a construction scheme of the targeting vector pNT3LNT obtained in Example 2. The abbreviations used in the figures are defined as follows.

From the mouse NT-3 genomic gene thus obtained, a DNA fragment was isolated between the unique EcoRV site in the coding region thereof and another EcoRV site 5.5 kb upstream of the former. This fragment was ligated to an SmaI cleavage fragment of plasmid pMC1871 (Pharmacia LKB, 27-4945-01) by T4 ligase, to obtain plasmid pEVlacZ. The direction of the insert was confirmed by the pattern of cleavage of pEVlacZ with restriction enzyme EcoRV. After the obtained plasmid pEVlacZ was cleaved with SalI, the resulting 9.5 kb fragment was isolated and ligated to an SalI site of pBluescript II SK+ (Toyobo, SC212205), to obtain plasmid pSKlacZ, which was then cleaved with NotI and SalI to obtain a 9.5 kb NotI-SalI fragment (fragment 1) (FIG. 1).

2) From the mouse NT-3 genomic DNA, a 3 kb DNA fragment was isolated between the unique SmaI site in the encoding region thereof and the 3'-terminal SalI site of the cloned mouse NT-3 genomic DNA. This fragment was ligated to plasmid vector pUC18, previously digested with SmaI and SalI, to obtain plasmid pUCSMS, which was then cleaved with HindIII and PstI to obtain a 1.0 kb HindIII-PstI fragment. Next, the NotI linker was ligated to pUC18 at the SmaI site to yield plasmid pUC18S⁻, uncleavable with restriction enzyme AvaI, which was treated with HindIII and PstI and ligated with the above isolated 1.0 kb HindIII-PstI fragment of mouse NT-3 genomic DNA, to obtain plasmid pUCHP. After pUCHP was cleaved with AvaI, its restriction enzyme cleavage sites were blunted with T4 polymerase. To this fragment, a DNA fragment, or an XhoI-EcoRI fragment containing a neomycin resistance gene expression unit isolated from pKJ2, was ligated a plasmid containing the neomycin resistance gene whose restriction enzyme cleavage ends were previously blunted with T4 polymerase, to obtain plasmid pHPNeo (the direction of insertion of the neomycin resistance gene is available).

Figure 2:
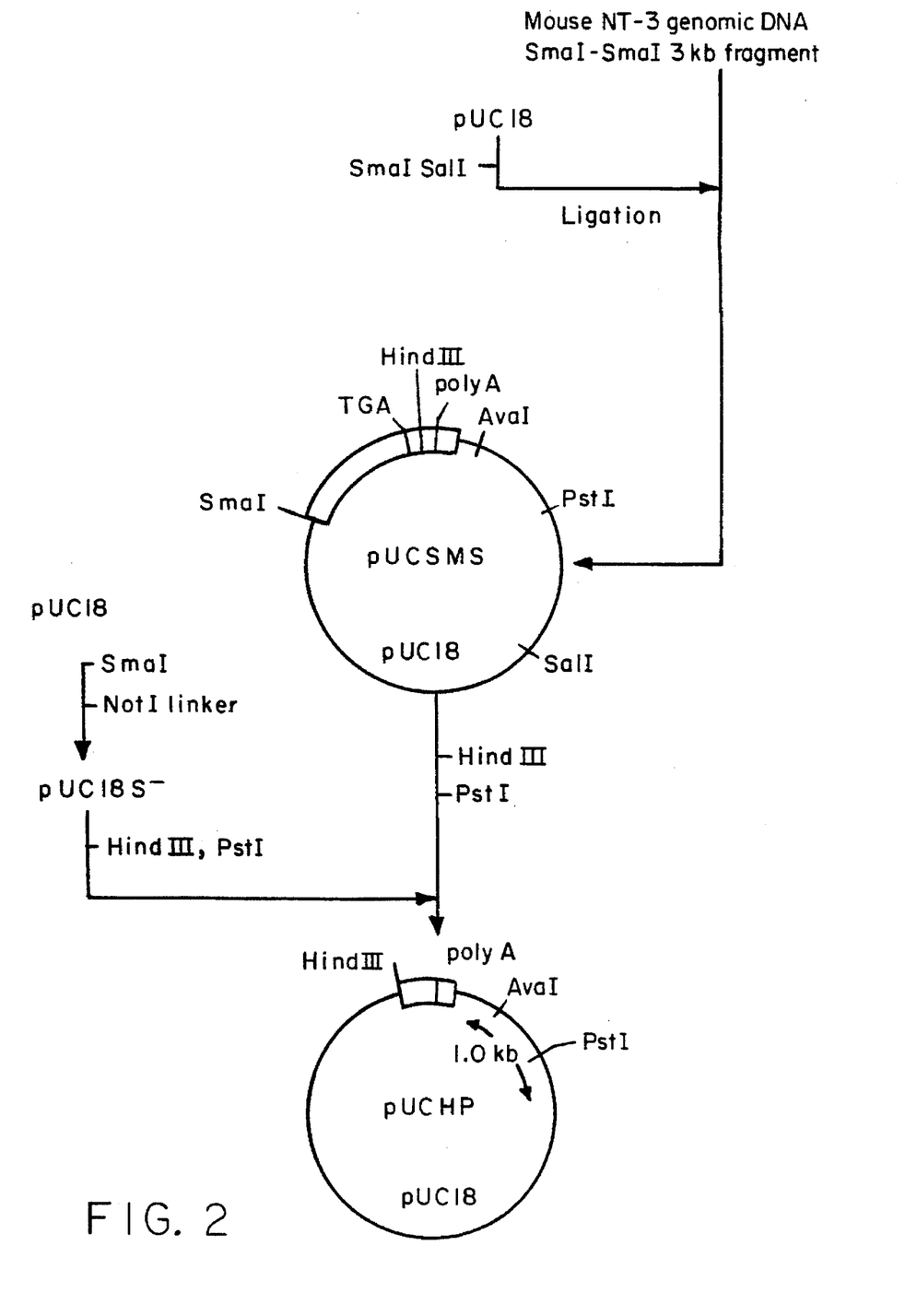
Figure 3:
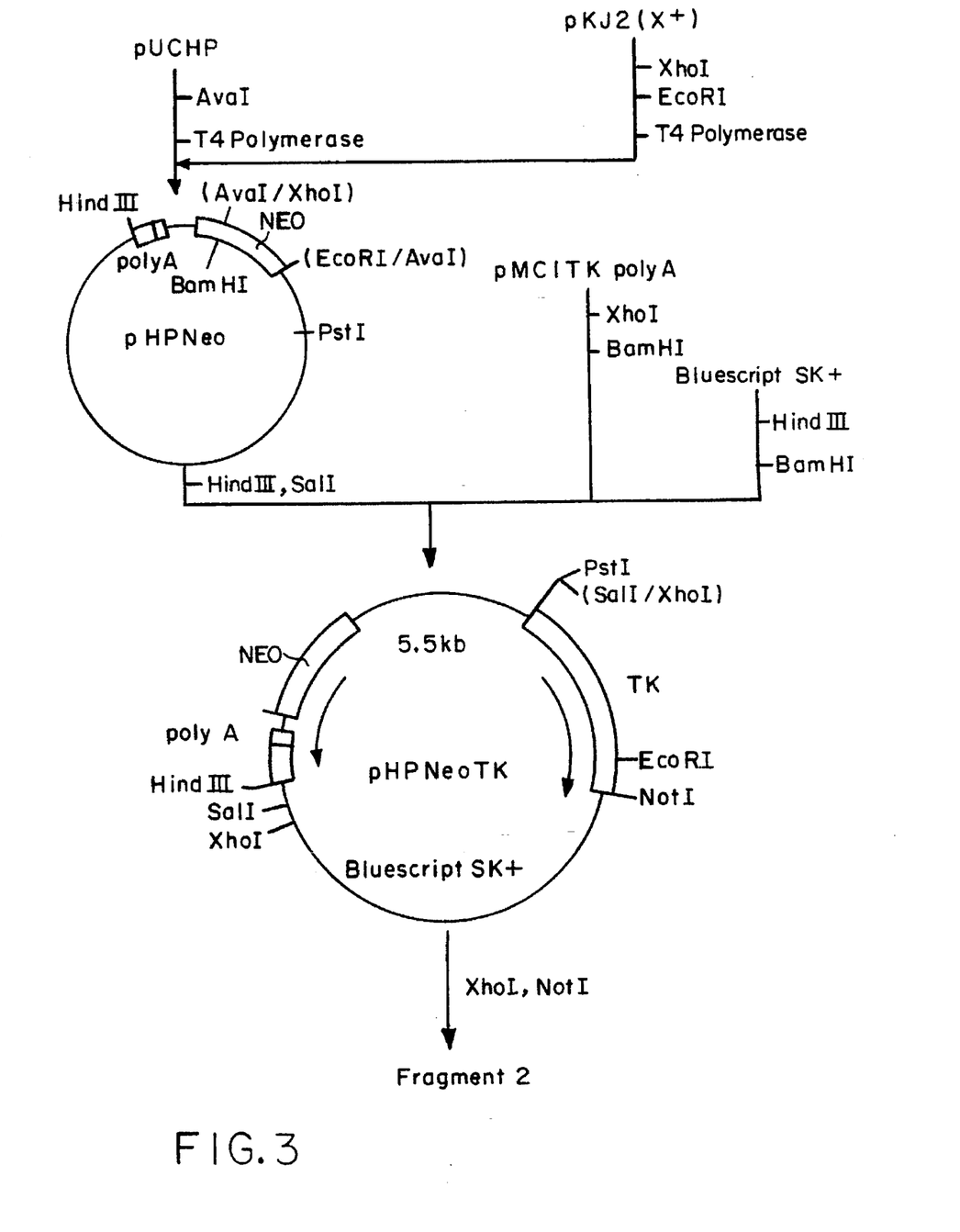

A 2.7 kb DNA fragment resulting from pHPNeo cleavage with HindIII and SalI, a 3.0 kb DNA fragment resulting from cleavage of plasmid pMC1TK polyA containing a herpes simplex virus thymidine kinase expression unit with XhoI and BamHI, and a fragment resulting from cleavage of pBluescript II SK+ with BamHI and HindIII were ligated together to obtain plasmid pHPNeoTK, which was cleaved with XhoI and NotI to obtain a 5.5 kb XhoI-NotI fragment, which was isolated (fragment 2) (FIGS. 2 and 3).

Figure 4:
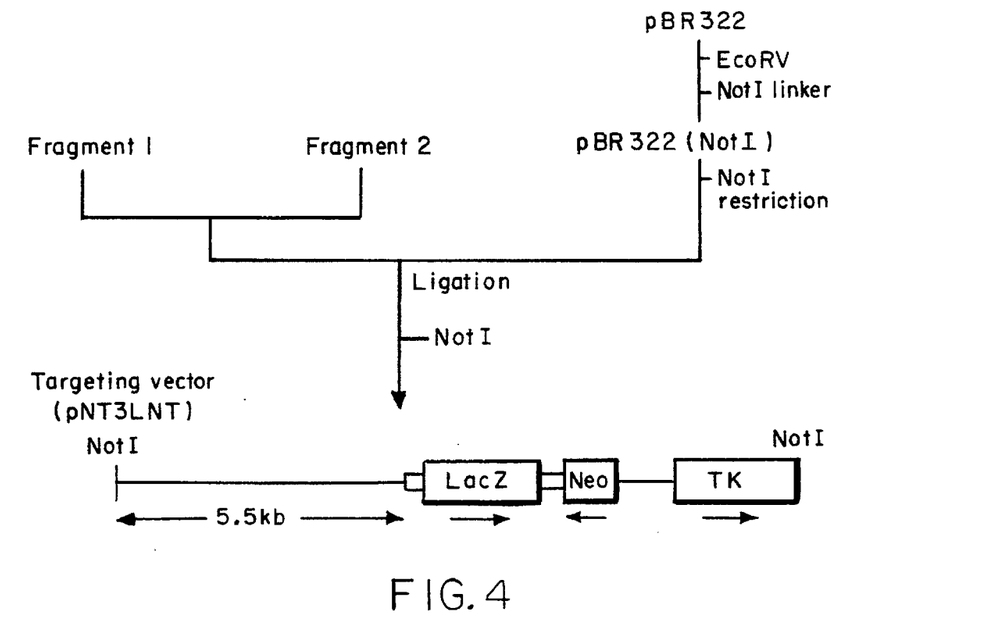

3) Plasmid vector pBR322 was cleaved with restriction enzyme EcoRV, followed by NotI linker ligation by means of T4 ligase, to obtain pBR322 (NotI), a plasmid vector capable of cloning a DNA fragment at NotI site. This plasmid vector pBR322 (NotI) was cleaved with NotI and ligated with previously prepared fragments 1 and 2 in 1) and 2) above to obtain plasmid pNT3LNT (FIG. 4). (It is also possible to use other vectors such as pBluescript vector or use a pUC plasmid vector as incorporating a NotI site.)

Figure 5:
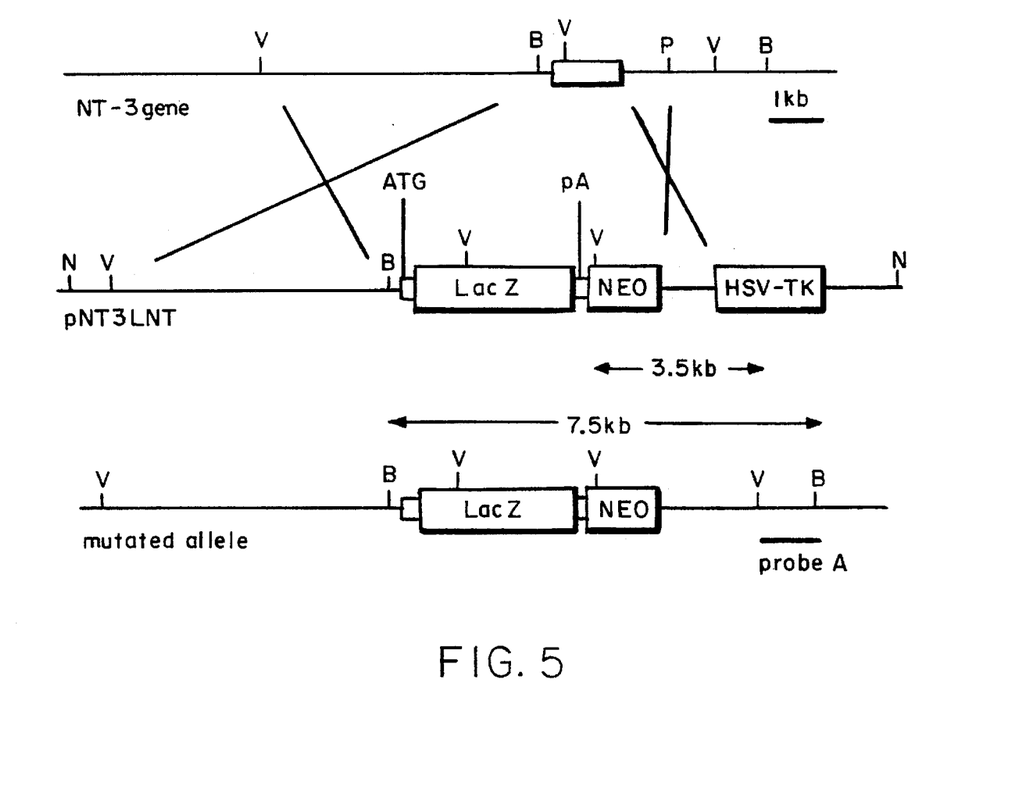
FIG. 5 shows a targeting construct incorporating mouse genomic DNA and the plasmid pNT3LNT obtained in Example 2, in which the intron is shown by a thin solid line and the exon by a bold solid line.
Figure 6:
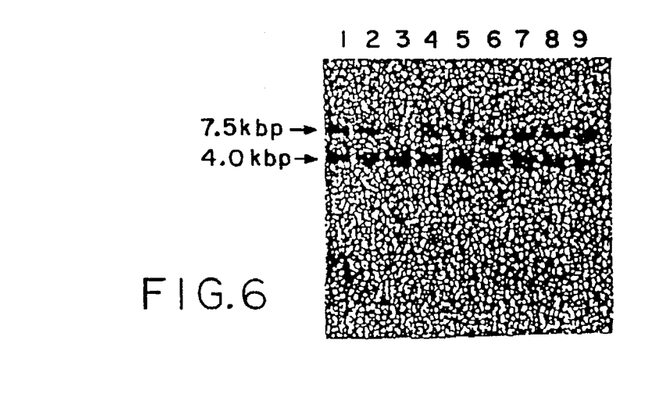
FIG. 6 shows results of Southern hybridization of the NT-3 disrupted ES cell line obtained in Example 3.

Example 3 Gene Introduction and Selection of ES Cells Deficient in the NT-3 Gene ES cell BDM-3, described in Example 1, grown almost confluently was trypsinized to single cells. After the reaction was stopped by addition of ES cell culture medium (ESM: DMEM, 20% inactivated FBS, 0.1 mM non-essential amino acids, 1.0 mM sodium pyruvate, 0.1 mM 2-ME, 0.1 mM nucleoside, $1\times10^3$ U/ml rmLIF), centrifuged, and the cell pellet was suspended in HEPES-buffered saline (21 mM HEPES, pH 7.5, 137 mM NaCl, 5 mM KCl, 0.7 mM $Na_2PO_4$, 1 g/l glucose). A targeting vector, cleaved out from the plasmid pNT3LNT obtained Example 2 by NotI, was purificated by phenol-chloroform extraction and ethanol precipitation. The precipitate was dissolved in HEPES-buffered saline. To the above ES cell suspension (0.5 ml), prepared to contain $5\times10^7$ cells, the above targeting vector was added to a final concentration of 10 µg/ml (for more efficient obtainment of gene-introduced cells, it is preferable that the vector is added to a final concentration of 100 µg/ml), and the ES cells were transfected by electroporation at 250 V and 960 µF using a gene pulser from Bio-Rad Laboratories. After electroporation, cells were seeded over 10 cm petri dishes at $3\times10^6$ cells per dish and cultured in ESM for 48 hours. Selection culture for ES cells deficient in the NT-3 gene was then initiated on the same medium but supplemented with G418 (200 µg/ml, GIBCO) and 1-(2-deoxy-2-fluoro-β-D-arabinofuranosyl)-5-iodouracil [FIAU; 0.2 µM, prepared as described in Nature, Vol. 344, p. 172 (1990)]. The medium was replaced with fresh every 2 days. Colonies which grew were collected at 9–11 days following selection culture initiation, and cultured one by one while the culture scale was increased. Thus obtained G418-resistant cells were judged as to NT-3 gene deficiency by extracting DNA from some colonies, digesting it with restriction enzyme BglII and performing Southern hybridization with a 1.0 kb EcoRV-BglII fragment prepared from mouse genomic DNA (FIG. 5) as probe A. In NT-3 gene disrupted cell lines, the band appeared at positions corresponding to 4.0 kbp and 7.5 kbp (FIG. 6). In contrast, the control wild type BDM-3 genelated a 4 kbp band alone. Electroporation of $1.2\times10^8$ ES cells yielded $5\times10^4$ colonies of a G418-resistant strain and $9.4\times10^3$ colonies of a strain resistant to both G418 and FIAU. The ratio of target clone concentration with FIAU was 5.3-fold. Southern hybridization analysis of these colonies revealed that mutation was induced in 23 clones. A targeting vector and mouse NT-3 locus are shown in FIG. 5. The NB4-71 cell line thus obtained, an ES cell line deficient in the NT-3 gene, has been deposited under accession number IFO 50404 at the Institute for Fermentation, Osaka (IFO) since Jul. 6, 1993, and under accession number FERM BP-4362 at the National Institute of Bioscience and Human-technology (NIBH), Agency of Industrial Science and Technology, Ministry of International Trade and Industry, under the Budapest treaty since Jul. 14, 1993.

Example 4 Generation of NT-3-Deficient Mice

Of the 23 clones of ES cell lines obtained in Example 3, in which the NT-3 gene is disrupted, 6 were individually injected to 8-cell embryos of the ICR mouse by the method of Tokunaga et al., [Saibo Kogaku, Vol. 10, p. 403 (1991)]. Specifically, after superovulation was induced by hormone administration by the method described in Example 1, the mouse was crossed with a male ICR mouse. 2.5 days later, 8-cell stage embryos of ICR mice, collected by uterine perfusion, along with cells, were placed in LIF-free ESM droplets covered with liquid paraffin in 6 cm petri dishes. To each host 8-cell stage embryo, 10–15 ES cells were injected by microinjection. About 10 such embryos were transplanted to both uterine horns of an ICR mouse, as an adoptive parent, at 2.5 days of pseudopregnoncy, prepared by crossing with a vasectmized male. The resulting chimeric mouse was back crossed with an ICR mouse; the offspring were examined for coat color to determine the potential of ES cells for differentiation into a germ cell line.

Figure 7:
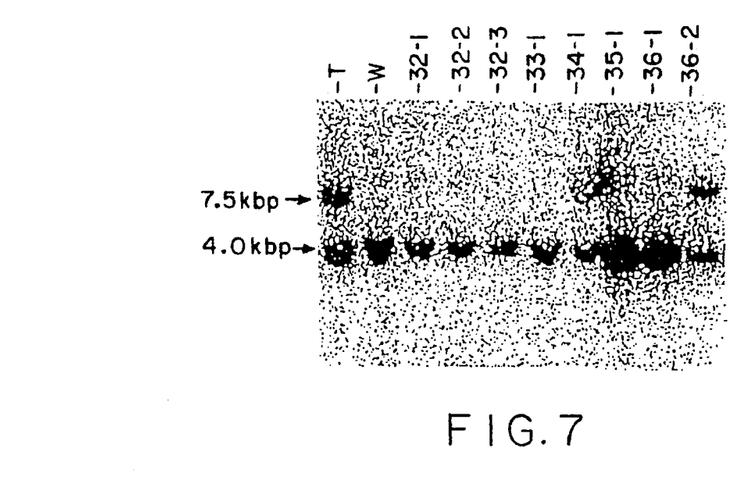
FIG. 7 shows results of Southern hybridization of the mouse deficient in NT-3 gene generated in Example 4, in which lane T shows the results on the NT-3 disrupted cell line, lane W those for normal (wild) ICR mouse DNA and lanes 32-1 through 36-2 those for individual numbers of offspring of a mouse deficient in expression of the NT-3 gene.

Twenty-three male and 8 female chimeric mice were obtained, of which 7 females from 2 strains of ES cells were germ cell line chimeric mice which pass the characters of ES cells to offspring. From these 7 chimeric mice, 81 offspring mice were born, of which 51 were analyzed by Southern hybridization by the method as in Example 3 (FIG. 7); 2 were identified as heterozygote mice.

Figure 8:
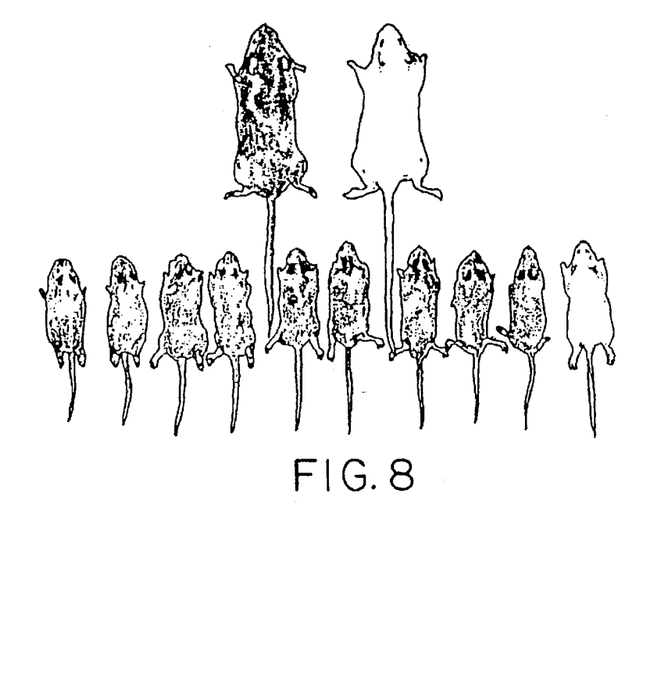
FIG. 8 shows mice, deficient in NT-3 expression of the germ line generated in Example 4.

FIG. 8 shows the results of crossing between a chimeric mouse (black, male) wherein the contribution of BDM-3 cells to the germ cell line was almost 100% and a normal ICR mouse (white, female). All offspring produced were found to be of ES cell origin, as shown in FIG. 8. The white offspring shown in the lower panel for reference is a pup from a normal ICR mouse.

Example 5 Characters of NT-3-Deficient Mice

Crossing of heterozygous NT-3 deficient mice yielded homozygous NT-3 deficient mice at a probability of about ¼. The homozygous NT-3 deficient mice showed almost normal development until delivery, but showed a high tendency toward sucking problem after birth. With this in mind, some wild or heterozygote mice of the same litter were eliminated to leave only 1 per mother, to allow the mother to suckle two or more homozygotes, whereby 10–20% of homozygous NT-3 deficient mice of sucking problem were allowed to survive. These mice developed gait disturbance around 1 week after birth.

Example 6 Application of NT-3-Deficient Mouse

The NT-3-deficient mouse prepared in Example 4 expresses lacZ in place of NT-3 in tissues where NT-3 is normally expressed, because the gene region encoding the NT-3 protein is partially replaced with lacZ derived from *Escherichia coil*. It is therefore possible to simply observe NT-3 expression sites in such mice by staining with a substrate of β-galactosidase.

A sample such as an NT-3-deficient mouse or a tissue section therefrom is fixed in glutaraldehyde and washed with PBS, followed by reaction with a staining solution X-gal-containing 5-bromo-4-chloro-3-indolyl-β-D-galactopyranoside (X-gal) (1 mM X-gal, 3 mM potassium ferricyanide, 3 mM potassium ferrocyanide, 1 mM magnesium chloride, 0.1% Triton X-100, 1×PBS) at room temperature or 37° C. for 30 minutes to 1 hour. The tissue specimen is washed with a 1 mM EDTA/PBS solution to stop the β-galactosidase reaction.

NT-3-deficient fetal mice were stained on a whole-mount basis by this method, to detect NT-3 expression. NT-3 was expressed in the mesencephalon, lower mandible and metameres at embryonic day at 10. With the progress of fetal development, NT-3 expression increased in these tissues, followed by strong expression in peripheral tissues such as eyes, limbs, external genitalia and bearded areas. There was no difference in lacZ expression pattern between NT-3-heterodeficient and NT-3-homodeficient mice. In tissue specimens at embryonic day 17, relatively intensive staining was seen in peripheral nerve terminal tissues such as vicinities of hair pores, irises, skeletal muscles, whisker pad, gastric walls, intestinal walls and vesical walls, peripheral nervous ganglia such as trigeminal and dorsal root ganglia, and central nervous tissues such as the cerebellum, mesencephalon and ventral horn motor neurons in spinal cords.

Example 7 Effect of NT-3 Deficiency on NT-3 Receptor Gene Expression in Mice Tissue specimens of the trigeminal and dorsal root ganglia of NT-3-homodeficient fetal mice (embryonic day at 17) were examined for the expression of trkC, an NT-3-specific receptor gene, by in situ hybridization in a conventional manner. In comparison with the wild-type mouse, the NT-3-homodeficient mouse showed markedly decreased trkC expression in these tissues. A mixture of thus obtained following three DNA strands were used as a probe for in situ hybridization of trkC.

| | |
|---|---|
| 5'-GATCTCAGTCTTGCTGCAGACACAATTTGCAGGGCAAGCCAGCAC-3' | (SEQ ID NO:3) |
| 5'-TGTGGTGAGCCGGTTACTTGACAAGTTTATATAACGCAAGTGGGG-3' | (SEQ ID NO:4) |
| 5'-CAAAGGAGAGCCAGAGCCATTGCAAGTGATCACGGCATTGTCTCC-3' | (SEQ ID NO:5) |

Figure 9:
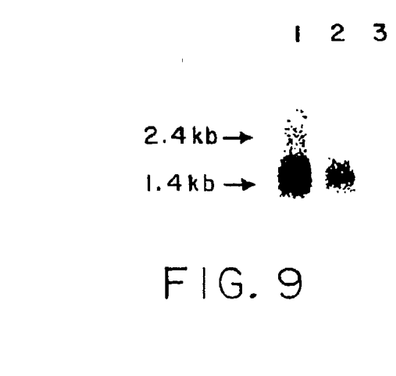
FIG. 9 shows the results of Northern blot analysis of NT-3 expression in the brain of an NT-3-deficient mouse.

Anatomical examination revealed that the trigeminal nerve of the homozygous NT-3 deficient mice had a volume about one-third of that of wild-type mice, with considerable reduction in sensory nerve cells. This sensory nerve disorder may be the major cause of sucking problem in newborn mice and hence a cause of gait disturbance. FIG. 9 shows the results of Northern blot analysis of NT-3 expression reduction in the brain of a 1-day-old NT-3 deficient mouse, using mRNA from a mouse brain. As shown in FIG. 9, the homozygous NT-3 deficient mouse (lane 3) showed no expression of NT-3. The heterozygous NT-3 deficient mouse (lane 2) expressed NT-3 at about half the mount expressed by the normal wild mouse (lane 1).

For probe, a part of trkC cDNA was obtained by RT-PCR. The sequences used for this RT-PCR were based on the sequence of rat trkC cDNA [Merlio, J. P., et al. Neuroscience vol. 51, pp.513–532, (1992)], which were 5'-AGCGTCTGGCTGGACTATGTGGGGCT-3' (SEQ ID NO:6) for the sense primer and 5'-GGTGACTATCCAGTCCACATCA-3' (SEQ ID No:7) for the antisense primer. The template mRNA was extracted from mouse brain. The obtained cDNA fragment was sequenced and three 45-mer, oligonucleotides were used for in situ hybridization.

What is claimed is:

1. A mutant mouse comprising a homozygous disruption in the endogenous neurotrophin-3 gene, wherein said mutation has been introduced by homologous recombination and results in the insertion of a reporter gene or a drug-resistance gene into an exon of the neurotrophin-3 gene and further wherein said mouse has a reduced number of sensory neurons compared with the number of sensory neurons in a mouse lacking said homozygous disruption.

2. The mouse of claim 1 wherein said reporter gene is an *Escherichia coil* β-galactosidase gene.

3. The mouse of claim 1, wherein expression of the reporter gene is under the control of a neurotrophin-3 promoter.

4. The mouse of claim 3, wherein the reporter gene is *Escherichia coli* lacZ.

5. A method of screening for a substance that enhances neurotrophin-3 promoter activity comprising:

administering the substance to be screened to the mouse of claim 3 and detecting expression of the reporter gene, wherein increased expression of said reporter gene in the presence of said substance indicates that said substance enhances neurotrophin-3 promoter activity.

6. The method of claim 5, wherein the reporter gene is an *Escherichia coli* β-galactosidase gene.

7. A mutant mouse comprising a homozygous disruption in the endogenous neurotrophin-3 gene, wherein said mutation has been introduced by homologous recombination and results in the insertion of an *Escherichia coil* β-galactosidase gene or a DNA segment encoding a gene product that confers resistance to neomycin into an exon of the neurotrophin-3 gene and further wherein said mouse has a reduced number of sensory neurons compared with the number of sensory neurons in a mouse lacking said homozygous disruption.

* * * * *